US006709680B1

(12) United States Patent
Yvin et al.

(10) Patent No.: US 6,709,680 B1
(45) Date of Patent: Mar. 23, 2004

(54) USE OF ISO-OSMOTIC SALINE SOLUTIONS, METHOD FOR PREPARING SAME AND CERUMENOLYTIC MEDICINES BASED ON SAID SOLUTIONS

(75) Inventors: Jean-Claude Yvin, Saint Malo (FR); Isabelle Cadulal, Plerguer (FR); Olivier Tabary, Reims (FR)

(73) Assignee: Laboratories Goemar S.A., Saint Malo (FR)

(*) Notice: Subject to any disclaimer, the term of this patent is extended or adjusted under 35 U.S.C. 154(b) by 0 days.

(21) Appl. No.: 09/743,010
(22) PCT Filed: Jun. 29, 1999
(86) PCT No.: PCT/FR99/01564
§ 371 (c)(1),
(2), (4) Date: Mar. 26, 2001
(87) PCT Pub. No.: WO00/00208
PCT Pub. Date: Jan. 6, 2000

(30) Foreign Application Priority Data

Jun. 29, 1998 (FR) .............................. 98 08249

(51) Int. Cl.⁷ ..................... A61K 33/00; A61K 33/06; A61K 33/14; A61K 33/20

(52) U.S. Cl. ..................... 424/680; 424/600; 424/677; 424/678; 424/679; 424/681; 424/682; 424/722; 514/956

(58) Field of Search ............... 424/680, 677, 424/678, 679, 681, 682, 722, 600; 514/956

(56) References Cited

U.S. PATENT DOCUMENTS 4,581,226 A * 4/1986 Dillon ..................... 514/886

FOREIGN PATENT DOCUMENTS

| EP | 747044 A | 12/1996 |
| FR | 2688133 | 9/1993 |
| FR | 2735980 | 1/1997 |

OTHER PUBLICATIONS

WPIDS abstract, accession No. 1997–111425 (1997).*

* cited by examiner

*Primary Examiner*—John Pak
(74) *Attorney, Agent, or Firm*—Kilpatrick Stockton LLP

(57) ABSTRACT

The invention concerns the use of iso-osmotic saline solutions, in particular obtained from sea water, to obtain a medicine for cerumenolytic treatment.

1 Claim, 2 Drawing Sheets

USE OF ISO-OSMOTIC SALINE SOLUTIONS, METHOD FOR PREPARING SAME AND CERUMENOLYTIC MEDICINES BASED ON SAID SOLUTIONS

This application is a 371 of PCT/FR99/01564, filed on Jun. 29, 1999.

The invention relates to a cerumenolytic medicine, that is a medicine which is suitable for dissolving cerumen plugs.

The invention is also directed toward the process for preparing this medicine.

It may be recalled that cerumen is a very fatty, yellow-brown substance which, on agglomerating, forms plugs and which is secreted by the sebaceous glands which line the external auditory meatus which links the pinna of the ear to the tympanic membrane.

The cerumen plugs cause buzzing in the ears and interfere with hearing.

Cerumenolytic medicines and preparations, that is products which are intended for dissolving existing cerumen plugs and preventing the formation of new plugs, are already known.

More specifically, a cerumenolytic preparation is known which is based on purified and sterilized sea water containing at least 36 g of salt per liter and which is marketed by DIEPHPA under the brand name AUDISPRAY.

While the existing cerumenolytic medicines and preparations are generally satisfactory, their efficacy leaves something to be desired.

The applicant company has now succeeded, after having carried out detailed research, in developing a cerumenolytic medicine whose efficacy is markedly superior to that of the cerumenolytic products which already exist.

The medicine according to the invention is characterized by the fact that it is based on an isoosmotic saline solution. This isoosmotic saline solution is characterized:
- by a pH of from 7.8 to 8.3
- by a density of from 1.008 and 1.01
- by a dry matter content of from 1 to 2% by weight, and
- by a chemical composition which is evident, as far as its main elements are concerned, from table A below:

TABLE A

| | |
|---|---|
| Solution (Na) | from 2000 to 2600 mg/l |
| Potassium (K) | from 40 to 80 mg/l |
| Chlorides (Cl) | from 5800 to 600 mg/l |
| Calcium (Ca) | from 300 to 400 mg/l |
| Magnesium (Mg) | from 1200 to 1500 mg/l |

Consequently, the invention lies in the use of an isoosmotic saline solution, which is in particular obtained from sea water, for obtaining a medicine which is intended for a cerumenolytic treatment.

This isoosmotic solution can be prepared in the manner described below.

Sea water, which is advantageously obtained from a depth of from 5 to 10 meters in an area where there are strong currents, and which is characterized by a salt content greater than 32 g/l, is used as the starting material.

This water is analyzed, decanted and then rapidly:
- de-sodium salted by the electrodialysis technique down to isotonicity, that is approximately 9 gram equivalents of sodium chloride per liter,
- filtered, and
- stored under sterile conditions in a stainless steel vat.

It is analyzed once again at this stage in order to check:
- its sterility,
- its isotonicity (physiological).

Finally, it is packaged in a sterile manner in specially treated premises in a controlled atmosphere.

The studies which demonstrated the cerumenolytic properties of isoosmotic saline solutions and their superiority vis a vis already existing cerumenolytic medicines and preparations will now be described.

In these studies, the cerumenolytic effect on human cerumen plugs was examined by determining the action on these plugs of, on the one hand, the isoosmotic saline solution employed in accordance with the invention and, on the other hand, the following known products, namely:
- that marketed by DIEPHA under the brand name AUDISPRAY, which product is a preparation based on purified and sterilized sea water,
- that marketed by the LCO Laboratory under the brand name C-FLUID, which product is a natural aqueous solution comprising calcium, sodium and magnesium salts in ionized form,
- that marketed by the Jean-Paul MARTIN Laboratories as a medicine under the brand name CERUMENOL, which product is an 80 to 0.5% solution of polysorbate,
- that marketed by the CHAUVIN SA Laboratory as a medicine under the brand name CÉRULYSE, which product contains xylene as the active principle,
- that marketed by the GILBERT Laboratories in the form of a hygiene preparation under the brand name A CÉRUMEN, which product is based on PEG 120 methylglucose betaine dioleate and alkylamidopolypeptide, TEA salt,
- that marketed by the CHAUVIN Laboratory in the form of a medicine sold under the brand name OTOLYSINE, which product is a medicine based on triethanolamine caprylate and caprylic acid.

Two series of experiments were performed; the first concerned cerumens from young adults and the second concerned cerumens from elderly subjects.

In the first series of experiments, quantities of in each case 0.1 g of cerumen plug were diluted, in hemolysis tubes and while incubating at 37° C., in, in each case, 5 ml of, on the one hand, the isoosmotic saline solution employed in accordance with the invention (solution A) and, on the other hand, of each of the products identified below, namely:

| | |
|---|---|
| AUDISPRAY | Solution B |
| C-FLUID | Solution C |
| CÉRUMENOL | Solution D |
| CÉRULYSE | Solution E |
| A CÉRUMEN | Solution F |
| OTOLYSINE | Solution G |

In the second series of experiments, the same procedure was adopted, using quantities of 0.1 g of cerumen in 5 ml of the isoosmotic solution employed in accordance with one part of the invention (Solution A') and, on the other hand, in 5 ml of the products identified below:

| | |
|---|---|
| AUDISPRAY | Solution B' |
| CÉRUMENOL | Solution D' |

| | |
|---|---|
| CÉRULYSE | Solution E' |
| A CÉRUMEN | Solution F' |
| OTOLYSINE | Solution G' |

In the two series of experiments, the lytic effect of the different solutions was analyzed (photographs taken at 0 min, 1 min, 3 min, 5 min, 15 min, 30 min and 45 min), it being understood that the tubes are inverted once before taking each photograph in order to render the dissociation of the plug visible.

In order to verify the lytic effect, and to find the optimum conditions for the photography, these experiments were repeated three times with smaller quantities of the material consisting of young patient plugs while preserving the abovementioned concentrations: in other words, quantities of 0.02 g were employed per 1 ml of cerumenolytic product.

Inspection of the corresponding photographs demonstrates the superiority of the isoosmotic saline solution employed in accordance with the invention.

The cerumenolytic effect of the isoosmotic saline solution employed in accordance with the invention, and of the cerumenolytic products of the prior art identified above, was also analyzed by densitometry (this involved analyses, performed using a BIORAD densitometer, of the numbered photeographic images corresponding to the different solutions A to G and A' to G'), with this being done in order to assess the cerumen plug-dissolving effect by examining the turbidity which appears in the tubes. The higher the magnitude of the densitometric value measured is, the more important the turbidity is and the higher the cerumenolytic effect is.

The results of the densitometric measurements are collated in tables B and C below.

Table B relates to the first assay series.

TABLE B

| Product tested | Results of the densitometric measurements | | | | | |
|---|---|---|---|---|---|---|
| | T = 0 | T = 3 | T = 5 | T = 15 | T = 30 | T = 45 |
| Solution A | 225 | 226 | 254 | 405 | 557 | 652 |
| Solution B | 232 | 235 | 267 | 310 | 464 | 510 |
| Solution C | 212 | 215 | 228 | 265 | 424 | 446 |
| Solution D | 207 | 225 | 260 | 397 | 524 | 590 |
| Solution E | 219 | 237 | 242 | 285 | 344 | 356 |
| Solution E | 197 | 210 | 241 | 320 | 383 | 398 |
| Solution G | 211 | 225 | 239 | 314 | 377 | 402 |

This table shows the densitometric value measured at time 0 (T=0), then after 3 min (T=3), 5 min (T=5), 15 min (T=15), 30 min (T=30) and 45 min (t=45) for each solution.

Table C, which is arranged in the same way as table B, collates the results of the second experimental series.

TABLE C

| Product tested | Results of the densitometric measurements | | | | | |
|---|---|---|---|---|---|---|
| | T = 0 | T = 3 | T = 5 | T = 15 | T = 30 | T = 45 |
| Solution A' | 218 | 226 | 254 | 297 | 352 | 378 |
| Solution B' | 183 | 183 | 223 | 233 | 235 | 244 |
| Solution D' | 189 | 189 | 190 | 224 | 290 | 350 |
| Solution E' | 185 | 185 | 185 | 190 | 205 | 211 |
| Solution F' | 170 | 170 | 193 | 199 | 207 | 211 |
| Solution G' | 183 | 183 | 183 | 205 | 210 | 244 |

The results collated in tables B and C clearly demonstrate the superiority of the isoosmotic saline solution according to the invention.

BRIEF DESCRIPTION OF THE DRAWINGS

For convenience in comparing the results which are collated in tables B and C, the results of these tables have been transposed to the graphs depicted in FIGS. 1 and 2, respectively, which graphs show the change in densitometry as a function of the time, expressed in minutes.

The novel cerumenolytic medicines according to the invention can be administered by spraying or by instillation, in the form of drops, into the external auditory meatus of the ear.

Figure 1:
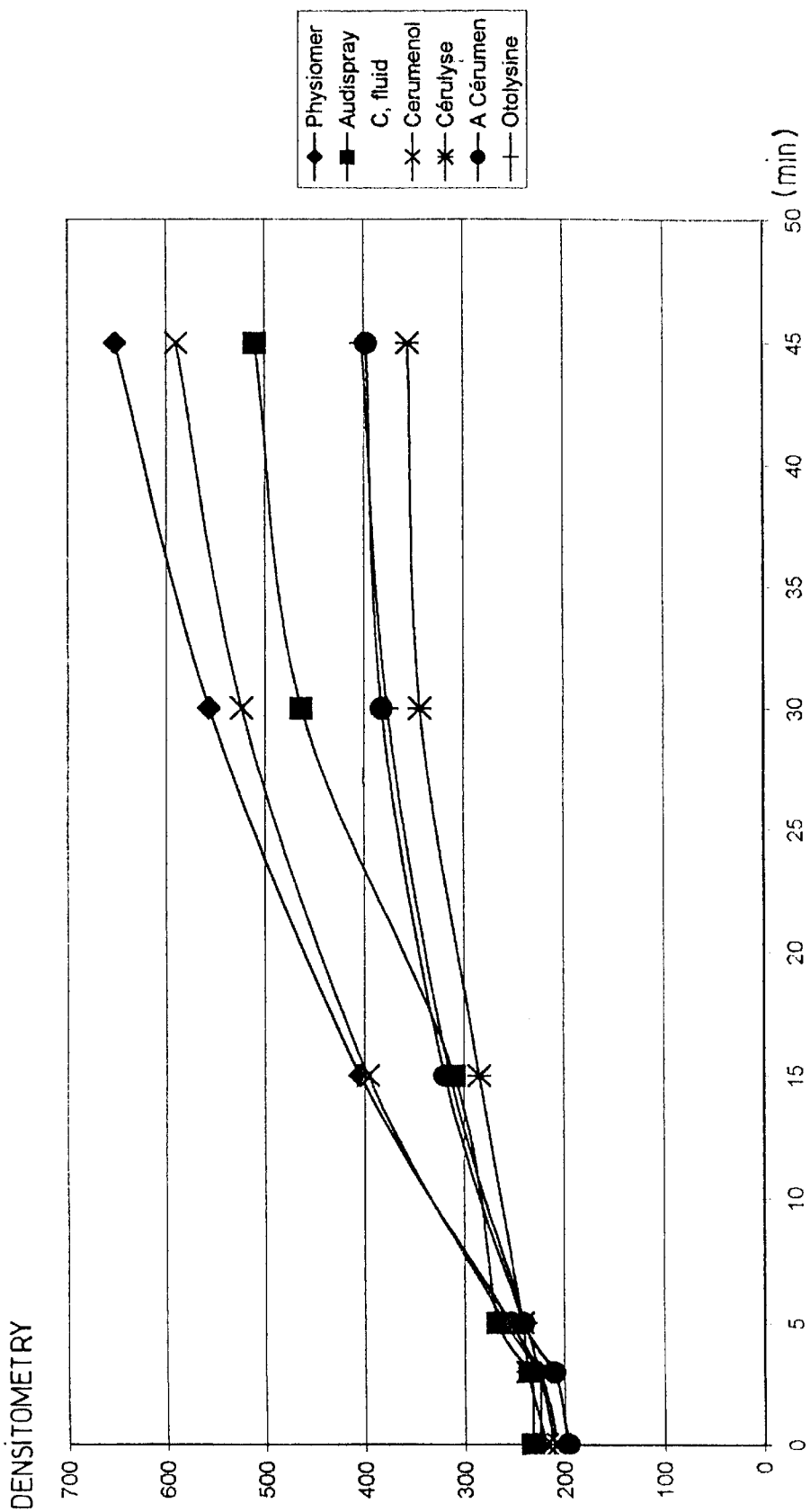
Figure 2:
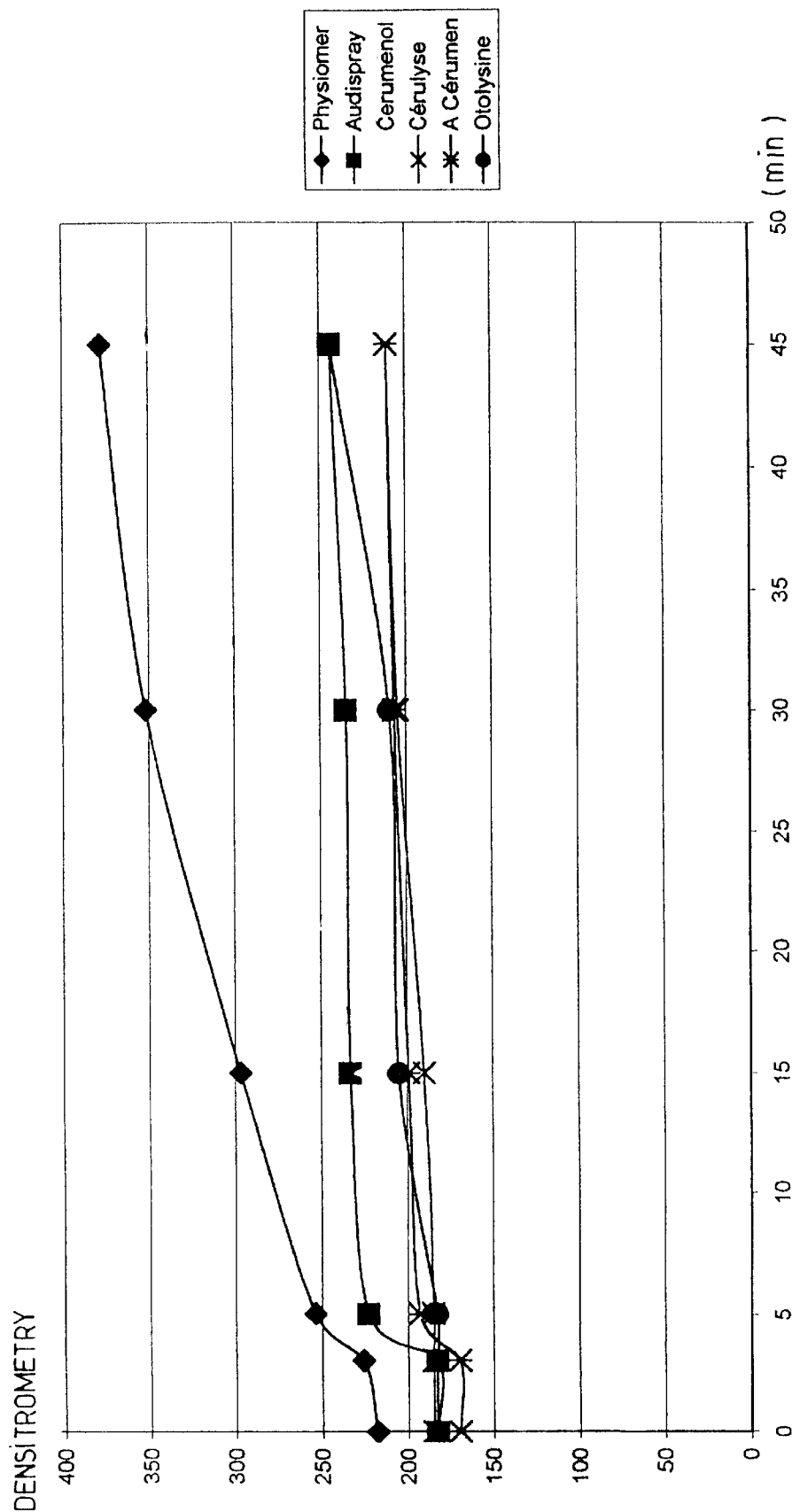

When cerumen plugs are present, the cerumenolytic medicines according to the invention can advantageously be administered at the rate of two sprayings or instillations per day over a period of from 3 to 4 days.

By way of regular hygiene, they can advantageously be administered two to three times a week, and more in the case of persons carrying hearing aids, in order to help keep the appliance in good working order.

What is claimed is:

1. A method of providing cerumenolytic treatment comprising administering, by spraying or by instillation in the form of drops, into an external auditory meatus of a person with cerumen plugs in the external auditory meatus, an isoosmotic saline solution obtained from sea water by electrodialysis, wherein the isoosmotic saline solution comprises sodium in a concentration of from 2,000 to 2,600 mg/l, potassium in a concentration of from 40 to 80 mg/l, chloride in a concentration of from 5,800 to 6,000 mg/l, calcium in a concentration of from 300 to 400 mg/l, and magnesium in a concentration of from 1,200 to 1,500 mg/l and further comprises;

a pH of from about 7.8 to about 8.3;
a density of from about 1.008 to about 1.01;
a dry matter content of from about 2% by weight; and
an osmolarity of from about 305 to 315 about mOs/kg.

\* \* \* \* \*